United States Patent
Weese et al.

(10) Patent No.: US 10,146,403 B2
(45) Date of Patent: Dec. 4, 2018

(54) MEDICAL IMAGE SYSTEM AND METHOD

(71) Applicant: KONINKLIJKE PHILIPS N.V., Eindhoven (NL)

(72) Inventors: Juergen Weese, Hamburg (DE); Irina Wächter-Stehle, Hamburg (DE); Axel Saalbach, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 738 days.

(21) Appl. No.: 14/345,023

(22) PCT Filed: Sep. 17, 2012

(86) PCT No.: PCT/IB2012/054913
§ 371 (c)(1),
(2) Date: Mar. 14, 2014

(87) PCT Pub. No.: WO2013/046090
PCT Pub. Date: Apr. 4, 2013

(65) Prior Publication Data
US 2015/0026643 A1    Jan. 22, 2015

Related U.S. Application Data

(60) Provisional application No. 61/539,023, filed on Sep. 26, 2011.

(51) Int. Cl.
*G16H 40/63* (2018.01)
*G06F 3/0482* (2013.01)
(Continued)

(52) U.S. Cl.
CPC ........ *G06F 3/0482* (2013.01); *G06F 3/04842* (2013.01); *G06F 19/321* (2013.01);
(Continued)

(58) Field of Classification Search
CPC ......... G06T 7/0012; G06T 2207/30004; A61B 2576/02; A61B 5/748; G06F 19/345; G06K 2209/051; G09B 23/30; G16H 40/63
(Continued)

(56) References Cited

U.S. PATENT DOCUMENTS 6,563,941 B1    5/2003    O'Donnell et al.
6,674,449 B1    1/2004    Banks
(Continued)

FOREIGN PATENT DOCUMENTS

DE    102010005170 A1    7/2011
JP    2001325294 A    11/2001
(Continued)

OTHER PUBLICATIONS

Duda, Richard O. et al "Use of the Hough Transformation to Detect Lines and Curves in Pictures", Graphics and Image Processing, Communications of the ACM, vol. 15, No. 1, Jan. 1972.
(Continued)

*Primary Examiner* — Andrew Tank

(57) ABSTRACT

System (100) for enabling an interactive inspection of a region of interest (122) in a medical image (102), the system comprising display means (160) for displaying user interface elements (310, 320, 330) of actions associated with the interactive inspection of the region of interest and a processor (180) for executing one of the actions when a user selects an associated one of the user interface elements, the system further comprising establishing means (120) for establishing the region of interest in the medical image, determining means (140) for determining an anatomical property (142) of the region of interest in dependence on an image property of the region of interest, and the display means (160) being arranged for (i), in dependence on the anatomical property,
(Continued)

establishing a display configuration (162) of the user interface elements, and (ii) displaying the user interface elements in accordance with the display configuration.

18 Claims, 3 Drawing Sheets

(51) Int. Cl.
    *G06F 19/00*     (2018.01)
    *G06F 3/0484*     (2013.01)
    *G06T 7/00*     (2017.01)

(52) U.S. Cl.
    CPC ........... *G06T 7/0014* (2013.01); *G16H 40/63* (2018.01); *G06T 2207/20104* (2013.01); *G06T 2207/30004* (2013.01)

(58) Field of Classification Search
    USPC .................. 382/128, 131, 132; 715/700, 810
    See application file for complete search history.

(56) References Cited

U.S. PATENT DOCUMENTS

| | | | |
|---|---|---|---|
| 7,031,504 B1 | 4/2006 | Argiro et al. | |
| 7,580,554 B2* | 8/2009 | Spahn | G06T 5/00 |
| | | | 382/128 |
| 7,664,298 B2* | 2/2010 | Lang | A61B 6/469 |
| | | | 382/128 |
| 8,244,007 B2 | 8/2012 | Breeuwer et al. | |
| 8,721,548 B2 | 5/2014 | Baba et al. | |
| 8,755,574 B2* | 6/2014 | Declerck | A61B 6/037 |
| | | | 382/128 |
| 2003/0200119 A1 | 10/2003 | Lewis | |
| 2004/0081343 A1 | 4/2004 | Takeo et al. | |
| 2004/0146204 A1 | 7/2004 | Ashton | |
| 2005/0238216 A1 | 10/2005 | Yoden | |
| 2006/0173858 A1 | 8/2006 | Cantlin | |
| 2007/0016016 A1 | 1/2007 | Haras et al. | |
| 2007/0078306 A1 | 4/2007 | Allison et al. | |
| 2007/0081700 A1 | 4/2007 | Blumenfeld et al. | |
| 2009/0028403 A1* | 1/2009 | Bar-Aviv | G06F 19/321 |
| | | | 382/128 |
| 2010/0067761 A1* | 3/2010 | Jakobsson | G06K 9/6209 |
| | | | 382/131 |
| 2010/0293505 A1 | 11/2010 | Kiefer et al. | |
| 2010/0322495 A1 | 12/2010 | Collet-Billon et al. | |
| 2010/0325269 A1 | 12/2010 | Kim | |
| 2010/0329529 A1* | 12/2010 | Feldman | G06K 9/6252 |
| | | | 382/131 |

FOREIGN PATENT DOCUMENTS

| | | |
|---|---|---|
| JP | 2002207992 A | 7/2002 |
| JP | 2000254127 A | 9/2003 |
| JP | 2003260061 A | 9/2003 |
| JP | 2006101900 A | 4/2006 |
| JP | 2006314778 A | 11/2006 |
| JP | 2007209583 A | 8/2007 |
| JP | 2007330374 A | 12/2007 |
| JP | 2005253770 A | 3/2014 |
| WO | 199949407 A1 | 9/1999 |
| WO | 03200119 A1 | 3/2003 |
| WO | 2008018014 A2 | 2/2008 |
| WO | WO 2009060355 A1 * | 5/2009 ......... G06F 19/3443 |

OTHER PUBLICATIONS

Tameem, Hussain Z et al "Morphological Atlases of Knee Cartilarge: Shape Indices to Analyze Cartilage Degradation in Osteoarthritic and Non-Osteoarthritic Population", Proceedings of the 29th Annual Int'l Conf. of the IEEE EMBS, Aug. 2007.

Ebadollahi, Shahram et al "Concept-Based Electronic Health Records: Opportunities and Challenges", MM'06 Oct. 2006.

The Ultimate in CT Productivity, Philips Brilliance Workspace Version 4.0, 2008.

Ecabert, O. et al "Towards Automatic Full Heart Segmentation in Computed-Tomography Images", Computers in Cardiology, vol. 32, pp. 223-226, 2005.

* cited by examiner

MEDICAL IMAGE SYSTEM AND METHOD

CROSS-REFERENCE TO PRIOR APPLICATIONS

This application is the U.S. National Phase application under 35 U.S.C. § 371 of International Application No. PCT/IB2012/054913, filed on Sep. 17, 2012, which claims the benefit of U.S. Provisional Patent Application No. 61/539,023, filed on Sep. 26, 2011. These applications are hereby incorporated by reference herein.

FIELD OF THE INVENTION

The invention relates to a system and method for enabling interactive inspection of a medical image. The invention further relates to a workstation, terminal and imaging apparatus comprising the system set forth, and a computer program product for causing a processor system to perform the method set forth.

In the field of medical imaging, certain regions of a patient's anatomy may be of particular interest to a clinician. For example, a clinician may need to inspect a medical image to assess whether a heart shown therein is healthy or diseased. Such an inspection may comprise performing a number of tasks at the hand of the medical image. For example, the clinician may need to first perform a coronary inspection, then a global left-ventricle analysis, and lastly draw up a report comprising a summary of the findings.

Medical systems exist that assist clinicians in such inspections, e.g., by displaying the medical image on a display and allowing the user to navigate through the medical image, allowing the user to manipulate the medical image, or by performing actions that are of relevance to the inspection. Such actions may comprise, e.g., analyzing certain aspects the region of interest, modifying display of the region of interest, performing measurements on the region of interest, including analysis results in a report, etc. These medical systems therefore allow a clinician to engage in an interactive inspection of the medical image by performing certain actions at the request of the user.

BACKGROUND OF THE INVENTION

A workstation 'Philips Brilliance Workspace 4.0', as described in www.healthcare.philips.com/pwc_hc/id_en/products/ct/products/ct_brilliance.sub.-64_channeVupdate/EBW.sub.-452296236551_LR.pdf, obtained on Jul. 18, 2011, comprises a user environment that provides access to several applications such as, e.g., cardiac analysis, stent planning, etc., with each of the applications offering a set of productivity features to the user. The document mentions that the manufacturer was focused on automating tasks and streamlining the applications to enable their use with a minimum number of mouse-clicks.

SUMMARY OF THE INVENTION

A problem of the above workstation is that the interactive inspection of a medical image involves too much interaction between the workstation and the user.

It would be advantageous to have a system or method for enabling interactive inspection of a medical image that involves less interaction with the user.

To address this concern, in a first aspect of the invention, a system is provided for enabling an interactive inspection of a region of interest in a medical image, the system comprising display means for displaying user interface elements of actions associated with the interactive inspection of the region of interest and a processor for executing one of the actions when a user selects an associated one of the user interface elements, the system further comprising establishing means for establishing the region of interest in the medical image, determining means for determining an anatomical property of the region of interest in dependence on an image property of the region of interest, and the display means being arranged for (i), in dependence on the anatomical property, establishing a display configuration of the user interface elements, and (ii) displaying the user interface elements in accordance with the display configuration.

In a further aspect of the invention, a workstation, a terminal and an imaging apparatus is provided comprising the system set forth.

In a further aspect of the invention, a method is provided of enabling an interactive inspection of a region of interest in a medical image, the method comprising displaying user interface elements of actions associated with the interactive inspection of the region of interest and executing one of the actions when a user selects an associated one of the user interface elements, the method further comprising establishing the region of interest in the medical image, determining an anatomical property of the region of interest in dependence on an image property of the region of interest, in dependence on the anatomical property, establishing a display configuration of the user interface elements, and displaying the user interface elements in accordance with the display configuration.

In a further aspect of the invention, a computer program product is provided comprising instructions for causing a processor system to perform the method set forth. The aforementioned measures provide a system and method in which user interface elements are displayed to the user which correspond to actions relating to the interactive inspection of a region of interest. The user may trigger execution of an action by selecting the corresponding user interface element. The action may directly relate to the interactive inspection, e.g., by being a part of said interactive inspection. For example, the action may involve performing an image analysis of the region of interest. The action may also indirectly relate to the interactive inspection, e.g., involving modifying the display of the medical image to allow the user to more easily perceive the region of interest therein. As such, the user may interactively perform the inspection by inspecting the region of interest on screen and by triggering the performing of certain actions relating to the inspection.

The region of interest is established in the medical image, e.g., by detecting the region of interest in the medical image, by receiving a location of the region of interest in the medical image, or by any other suitable means. Furthermore, an anatomical property of the region of interest is determined. The anatomical property relates to a property of the region of interest within the anatomy of the subject of the medical image. In order to determine the anatomical property, an image property of the region of interest is used. The image property is a property of the image data of the region of interest. Having established the anatomical property, a display configuration of the user interface elements is determined. The display configuration specifies a manner in which the user interface elements are displayed. Finally, the user interface elements are displayed in the aforementioned manner.

The measures according to the present invention have the effect that a user is presented with user interface elements that are displayed in a manner that is determined by an anatomical property of a region of interest in the medical image. Therefore, the anatomical property of the region of interest affects the manner in which the user interface elements are displayed. Moreover, by displaying the user interface elements in the aforementioned manner, the manner of selection of the user interface elements by the user is affected.

The anatomical property is typically of medical relevance, and thus will affect what actions the user selects, in which order the actions are selected, etc. By displaying the user interface elements in dependence on the anatomical property, the display of the user interface elements is adapted to said selection of the actions by the user. Advantageously, the display of the user interface elements is dynamically adapted to the particular anatomical property of the region of interest at hand, and is therefore not static.

Optionally, the display configuration specifies a structure of the user interface elements for establishing a prominence of individual ones of the user interface elements when being displayed. By specifying a structure of the user interface elements in dependence on the anatomical property, the mutual relationship between the user interface elements is established in dependence on said anatomical property. The mutual relationship between the user interface elements affects the prominence of individual ones of the user interface elements, and as a result, the prominence of said individual ones of the user interface elements is affected or determined by the anatomical property of the region of interest. Here, the term prominence refers to a visual conveying of the relative importance of the individual ones of the user interface elements when being displayed to the user.

Optionally, the structure of the user interface elements comprises at least one of: a rank of the user interface elements in a list, a hierarchical arrangement of the user interface elements in a menu tree, and a spatial arrangement of the user interface elements on a display area. A rank of user interface elements in a list is well suited for conveying the prominence of the individual ones of the user interface elements to the user. A hierarchically arrangement of user interface elements in a menu tree allows conveying said prominence by arranging relevant user interface elements at a top of the menu tree and arranging less relevant user interface elements in a branch of the menu tree. A spatially arrangement of user interface elements on a display area allows conveying said prominence by arranging relevant user interface elements in a prominent part of the display area and arranging less relevant user interface elements in a less prominent part of the display area.

Optionally, the system is arranged for accessing medical data specifying a correspondence between the anatomical property and the actions, and the display means is arranged for establishing the display configuration in further dependence on the correspondence. Said medical data provides a correspondence between the anatomical property and the actions, and consequently of their associated user interface elements. This correspondence is taken into account when displaying the user interface elements.

Optionally, the display means is arranged for guiding the user through a medical workflow by establishing the display configuration in further dependence on a user's position in the medical workflow. It is common to follow a medical workflow during the interactive inspection of a region of interest. By establishing the display configuration in further dependence on the user's position in the medical workflow, the displaying of the user interface elements is adapted to the current position of the user in the medical workflow.

Optionally, the display configuration specifies a visibility of individual ones of the user interface elements in dependence on the user's position in the medical workflow. Advantageously, user interface elements of actions that are less or not relevant to said position in the workflow can be hidden. Advantageously, the user may only be shown user interface elements of actions that are relevant to his current position in the workflow.

Optionally, the actions associated with the interactive inspection of the region of interest are comprised in applications being executable on the processor, wherein each of the applications causes the display means to establish a different display configuration of the associated user interface elements, and wherein the system is arranged for, in dependence on the anatomical property, selecting one of the applications for execution. The displaying of the user interface elements is thus provided by applications that are selected and executed on a processor in dependence on the anatomical property.

Optionally, the actions comprise at least one of: adjusting display of the region of interest, performing a measurement on the region of interest, performing image processing on the region of interest, and including information pertaining the region of interest in a report. Said actions are of relevance in an interactive inspection of a region of interest.

Optionally, the determining means is arranged for determining the anatomical property by comparing the image property of the region of interest to a reference image property of a reference region of interest to establish the anatomical property as being indicative of a deviation of the region of interest with respect to the reference region of interest. A deviation of the region of interest with respect to a reference region of interest is typically of particular medical relevance.

Optionally, the detection means is arranged for determining the anatomical property by applying a Hough transform to the region of interest, comprising using a first Hough table and a second Hough table, the first Hough table being constructed from regions of interests having the anatomical property, the second Hough table being constructed from regions of interests not having the anatomical property, and comparing Hough accumulators of both Hough tables. Said transform is an efficient technique for determining the deviation of the region of interest with respect to a reference region of interest.

Optionally, the region of interest is an organ, and the anatomical property is indicative of the deviation in at least one of: a shape, a size, a texture and a location, of the organ. Deviations in the shape, size, texture or location of an organ with respect to a reference organ are typically of particular medical relevance.

It will be appreciated by those skilled in the art that two or more of the above-mentioned options, implementations, and/or aspects of the invention may be combined in any way deemed useful.

Modifications and variations of the imaging apparatus, the workstation, the terminal, the method, and/or the computer program product, which correspond to the described modifications and variations of the aforementioned system, can be carried out by a person skilled in the art on the basis of the present description.

A person skilled in the art will appreciate that the system may be applied to multi-dimensional image data, e.g. to two-dimensional (2-D), three-dimensional (3-D) or four-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), Nuclear Medicine (NM), Electron Microscopy (EM), and Optical Microscopy (OM), as well as multi-modality image data comprising a combination of any of the aforementioned modalities. A dimension of the multi-dimensional image data may relate to time. For example, a four-dimensional image may comprise a time domain series of three-dimensional images.

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
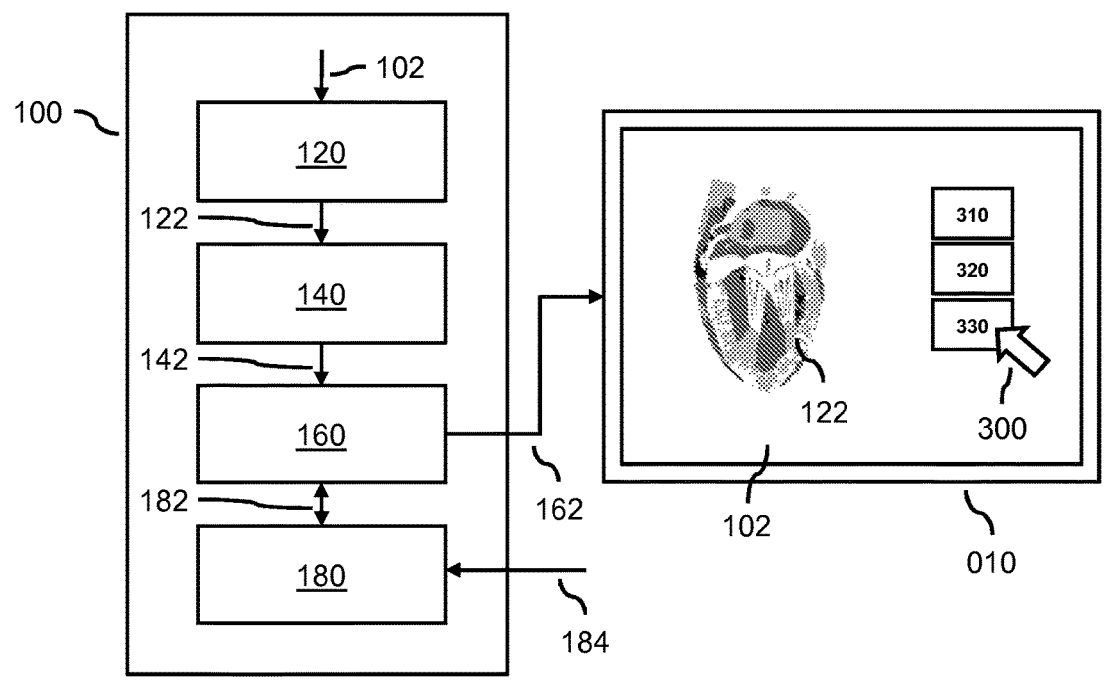
FIG. 1 shows a system according to the present invention.

FIG. 1 shows a system 100 for enabling an interactive inspection of a region of interest 122 in a medical image 102. The system 100 comprises an establishing means 120 for establishing the region of interest 122 in the medical image 102. For that purpose, the establishing means 120 is shown to receive the medical image 102 from within the system 100. Although not shown in FIG. 1, the medical image 102 may be received from a storage device. Alternatively, the medical image 102 may be received from outside the system 100. The system 100 further comprises a determining means 140 for determining an anatomical property 142 of the region of interest 122 based on an image property of the region of interest 122. The determining means 140 is shown to be connected to the establishing means 120 for receiving the region of interest 122 from the establishing means 120.

The system 100 further comprises a displaying means 160 for displaying user interface elements 310, 320, 330 of actions associated with the interactive inspection of the region of interest 122. For said displaying, the displaying means 160 is shown to be connected to a display 010. The display 010 is shown in FIG. 1 to be an external display, i.e., not being part of the system 100. Alternatively, the display 010 may be part of the system 100. The system 100 further comprises a processor 180 for executing one of the actions when a user selects an associated one of the user interface elements 310, 320, 330. For that purpose, the processor 180 is shown to receive selection data 184. The selection data 184 may be generated by a user interface device (not shown in FIG. 1), e.g., a mouse, allowing the user to select the user interface element by clicking with a cursor 300 on the user interface element 330. Alternatively, the user interface device may be a keyboard, touch screen, etc.

The display means 160 is arranged for, in dependence on the anatomical property 142, establishing a display configuration 162 of the user interface elements. For receiving the anatomical property 142, the display means 160 is shown to be connected to the determining means 140. The display means 160 is further arranged for displaying the user interface elements 310, 320, 330 in accordance with the display configuration 162, and for that purpose, is shown to provide the display configuration 162 to the display 010.

Here, the term display configuration refers to data for establishing a prominence of individual ones of the user interface elements when being displayed. For establishing a prominence of said user interface elements, the display configuration may specify one, or multiple of, e.g., a structure of the user interface elements, an arrangement of the user interface elements, a visibility of the user interface elements, etc. The structure may relate to a rank in a list, a hierarchical arrangement in a menu tree, a spatial arrangement on a display area, etc. The visibility of the user interface elements may relate to hiding or showing one or multiple ones of the user interface elements or to adjusting their size, color, etc.

Figure 2:
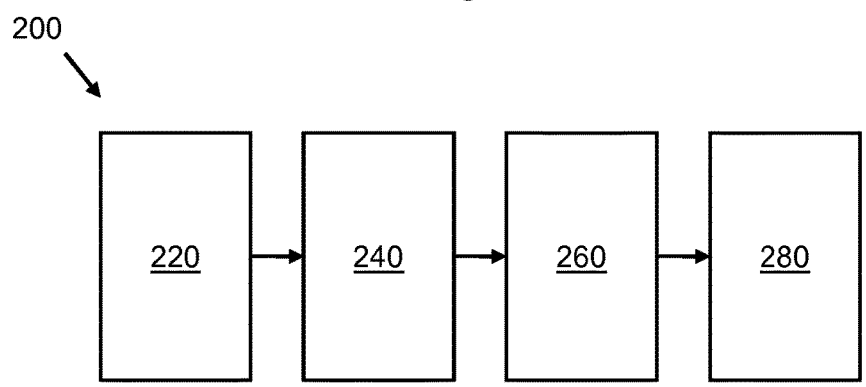
FIG. 2 shows a method according to the present invention.

FIG. 2 shows a method 200 of enabling interactive inspection of a region of interest in a medical image, the method comprising displaying user interface elements of actions associated with the interactive inspection of the region of interest and executing one of the actions when a user selects an associated one of the user interface elements, the method further comprising establishing 220 the region of interest in the medical image in a "ESTABLISHING THE REGION OF INTEREST" step, determining 240 an anatomical property of the region of interest in dependence on an image property of the region of interest in a "DETERMINING THE ANATOMICAL PROPERTY" step, establishing 260, in dependence on the anatomical property, a display configuration of the user interface elements in a "ESTABLISHING THE DISPLAY CONFIGURATION" step, and displaying 280 the user interface elements in accordance with the display configuration in a "DISPLAY USING THE DISPLAY CONFIGURATION" step. The method 200 may correspond to an operation of the system 100, and will be further explained in reference to the system 100. It will be appreciated, however, that the method may be performed in separation of said system.

Figure 3A:
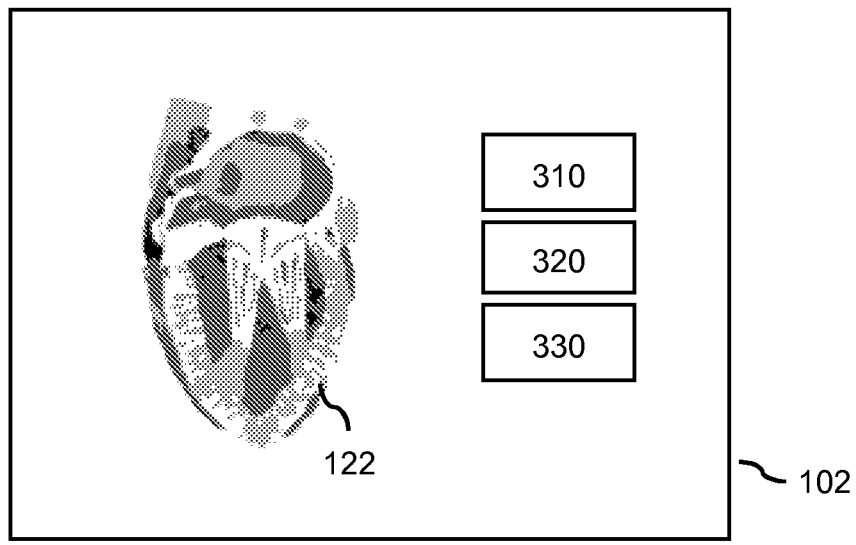
FIG. 3a shows a normal heart and user interface elements being displayed in a list in dependence on an anatomical property of the heart.

The aforementioned operation of the system 100 enables interactive inspection of a region of interest 122 in a medical image 102. An example of such an operation is shown in FIG. 3a. Here, a medical image 102 is shown comprising an organ as the region of interest, i.e., a heart 122. The establishing means 120 may establishing the heart 122 in the medical image 102 by using a segmentation algorithm as is known from the field of medical image analysis. Having established the heart 122 in the image, the determining means 140 may determine an anatomical property of the heart 122 based on an image property of the heart 122. For example, the determining means may determine a size of the heart 122 using a location of one or more luminance edge(s) in the image data of the heart, with the luminance edge(s) representing a delineation of the heart 122 in the medical image 102.

Having established the size of the heart 122, the display means 160 may establish a display configuration of the user interface elements 310, 320, 330 using the size of the heart 122. In this example, the size of the heart 122 may be compared to an expected size of a normal heart, and it may be determined that the size of the heart 122 in the medical image 102 substantially equals the expected size of the normal heart. As such, the display means 160 may establish a display configuration that shows the most relevant user interface elements 310, 320, 330 in an order that corresponds to a typical order of performing the actions associated with interactively inspecting a normally appearing and thus likely healthy heart. Moreover, the display configurations may hide user interface elements that are not or less relevant to the interactive inspection of a normally appearing heart.

Figure 3B:
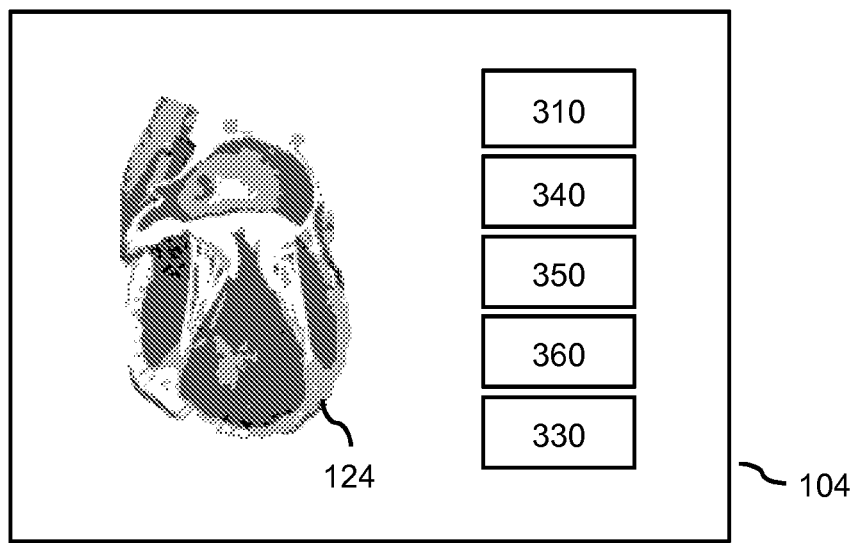
FIG. 3b shows an abnormal heart and user interface elements being displayed in a list in dependence on the anatomical property of the heart.

Another example of the operation of the system 100 is shown in FIG. 3b. Here, also a heart 124 is shown as the region of interest. However, in contrast to the heart 122 shown in FIG. 3a, the heart 124 shown in FIG. 3b corresponds to that of a heart failure patient. A medical indication for heart failure is an increase in size of the heart 124. The determining means may determine the size of the heart 124 using the aforementioned presence and location of one or more luminance edges in the image data of the heart.

Having established the size of the heart 124, the display means 160 may establish a display configuration of user interface elements using the size of the heart 124. In this example, the size of the heart 124 in the medical image 104 is substantially larger than an expected size of a normal heart, and may in fact correspond to an expected size of a heart failure patient. As such, the display means 160 may establish a display configuration that shows additional user interface elements 340, 350, 360 that are relevant for the interactive inspection of heart failure. Moreover, a user interface element 320, which may otherwise be displayed during the interactive inspection of a normal heart, may be hidden. Moreover, the order of the user interface elements 310, 340, 350, 360, 330 may be adapted to the typical order of performing actions associated with inspecting a heart of a heart failure patient.

Figure 4A:
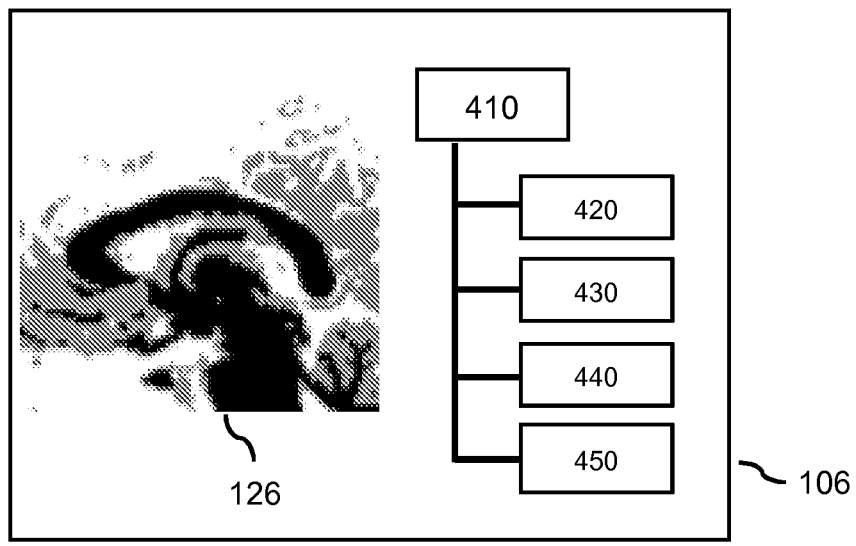
FIG. 4a shows a normal brain region and user interface elements being displayed in a menu tree in dependence on an anatomical property of the brain region.

FIG. 4a shows a similar example as was shown in FIG. 3a. However, here the region of interest is a brain region 126, the anatomical property is a thickness of a Corpus Callosum in the brain region 126, and the medical image 106 shown in FIG. 4a shows a brain region 126 without trauma, i.e., having a normal thickness of the Corpus Callosum. In accordance with the normal thickness, a display configuration of the user interface elements 410, 420, 430, 440, 450 may be established that arranges the user interface elements in a menu tree, with the user interface element 410 forming a top of the menu tree and the remaining user interface elements forming a branch in the menu tree. In this example, the user interface element 410 may be a user interface element that is most relevant to the interactive inspection of a Corpus Callosum having a normal thickness, and the user interface elements 420, 430, 440, 450 may be less relevant for said interactive inspection.

Figure 4B:
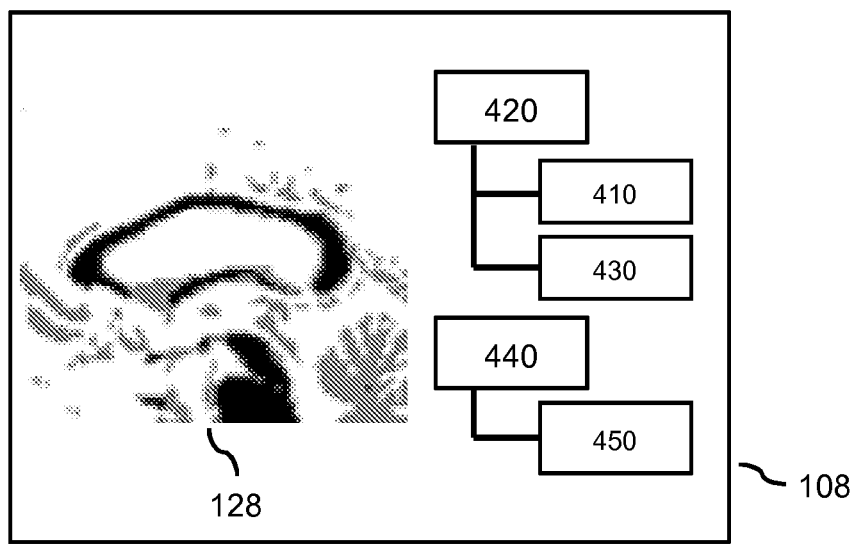
FIG. 4b shows an abnormal brain region and user interface elements being displayed in a menu tree in dependence on the anatomical property of the brain region.

FIG. 4b shows a brain region 128 which is traumatized. As a consequence, there is a thinning of the Corpus Callosum visible in the medical image 108. In accordance with the thinning, a display configuration of the user interface elements 410, 420, 430, 440, 450 may be established that differs from the configuration of said user interface elements shown in FIG. 4a. Here, two menu trees are provided, with the user interface element 420 forming a top of a first menu tree and another user interface element 440 forming a top of a second menu tree. The remaining user interface elements 410, 430, 450 are arranged in the respective menu trees below said user interface elements. Thus, the arrangement of the user interface elements takes into account the thinning of the Corpus Callosum by rearranging the user interface elements with respect to a Corpus Callosum having a normal thickness.

In the above, the term interactive inspection refers to an inspection wherein actions relating to the inspection are performed by the user and by the system at the request of the user. For example, when the medical image is a three-dimensional medical image, the user may visually inspect a region of interest therein, and as part of the inspection, request the system to segment the region of interest, calculate the volume of the region of interest and include the calculated volume in a report concerning the region of interest.

The establishing of the region of interest in the medical image may be performed in various ways. For example, the region of interest may be automatically detected in medical image using any known technique from the field of medical image analysis. The technique may be a segmentation technique. For example, the region of interest may be detected using seed-point based image growing segmentation, in which a seed is placed on an expected location of the region of interest, and image growing is used to obtain a segmentation of the region of interest. Alternatively, or in addition, the region of interest may be established by receiving location information of the region of interest, thereby providing the system with the location of the region of interest within the medical image. The location information may be provided by the user, e.g., by manually segmenting the region of interest in the medical image prior to performing the interactive inspection.

In the determining of the anatomical property of the region of interest in dependence on an image property of the region of interest, the term image property refers to a property present in, or directly derived from, the image data of the region of interest. For example, the image property may refer to one or more luminance values of pixels in the image data, or to an edge in the image data representing an outer boundary of the region of interest. The anatomical property is at least partly derived from the image property, and may provide an anatomical interpretation of the image property. For example, the image property may be an edge delineating the region of interest, and the anatomical property may be a size of the region of interest. Similarly, the image property may be a width of an area, and the anatomical property may be a thickness of a Corpus Callo sum in a brain. The image property may also be a texture in the region of interest, and the anatomical property may be a type of tissue represented by texture. It will be appreciated, however, that in order to determine the anatomical property, more information may be used than said image property. As a result, the correspondence between image properties and anatomical properties may not form a bijection. For example, other image properties may be used in determining the anatomical property, or metadata accompanying the medical image, etc.

The anatomical property may be indicative of a deviation of the region of interest with respect to a reference region of interest, i.e., a region of interest that is considered as basis or as template. The reference region of interest may have a reference image property, i.e., an image property that is associated with the reference region of interest. The determining means may be arranged for determining the deviation of the region of interest by comparing the image property to the reference image property. It will be appreciated that said comparing may be done without needing a medical image comprising the reference region of interest, as only the reference image property is needed in said comparing. Moreover, the reference image property may be obtained by averaging image properties of multiple regions of interest, and thus may not originate from a single region of interest or single medical image. Alternatively, the anatomical property may not be indicative of a deviation of the region of interest per se, but instead may be primarily an absolute instead of relative measure. For example, the anatomical property may relate to the size, shape, texture or location of the region of interest within the medical image, without necessarily denoting any deviation with respect to a reference.

The region of interest may be an organ, e.g., a heart, a liver, etc. The region of interest may also be an organ region, e.g., a region in the brain comprising the Corpus Callosum. The deviation of the region of interest may be a deviation in size of the region of interest, i.e., indicating whether the region of interest is larger or smaller than the reference region of interest. The deviation of the region of interest may also be a deviation in shape of the region of interest, e.g., indicating whether the region of interest is deformed with respect to the reference region of interest. The deviation may be determined by comparing the image property with the reference image property. The comparing may comprise determining a difference between said properties, or determining a similarity between said properties. Hence, determining a deviation in shape of the region of interest may comprise determining a similarity between the image property and an abnormal reference image property, or determining a difference between the image property and a normal reference image property.

The deviation of the region of interest may indicate a degree or probability of deviation, e.g., a 'score'. Thus, the comparing of the image property with the reference image property may yield a non-binary value. Alternatively, the deviation of the region of interest may correspond to a binary value indicating whether or not the region of interest deviates from the reference region of interest. The deviation of the region of interest may be associated with a medical finding. For example, the deviation of the region of interest may indicate whether the region of interest resembles most a normal, e.g., healthy, region of interest, or an abnormal, e.g., diseased, region of interest. For example, when the region of interest is a heart, the deviation may indicate whether the heart resembles most a healthy heart or a diseased heart. For that purpose, the reference region of interest may correspond to a healthy region of interest or to a diseased region of interest.

The deviation of the region of interest may be obtained by comparing the image property with a first reference image property and a second reference image property, with each reference image property originating from or corresponding to different reference regions of interest. For example, the image property may be compared to a first reference image property corresponding to a healthy region of interest as well as to a second reference image property corresponding to a diseased region of interest. As such, it may be determined whether the region of interest resembles most the healthy or the diseased region of interest. As another example, reference image properties may be used that correspond to different types of normal hearts, e.g., of adults and of children, and/or to different types of abnormal hearts, e.g., suffering from different diseases or being in different stadia of a disease. Thus, the determining of the deviation may take into account the diversity in patients and diseases.

The deviation of the region of interest may also be obtained by comparing a plurality of image properties to an associated plurality of reference image properties. For example, one of the plurality of image properties may relate to a texture of the region of interest, another one may relate to a contrast of the region of interest, etc. As such, the plurality of image properties may be seen as a multi-dimensional vector corresponding to the image properties of the region of interest. Obtaining the deviation of the region of interest may comprise comparing the multi-dimensional vector of image properties to a further multi-dimensional vector of reference image properties, e.g., by using any known technique from the fields of geometric algebra and vector algebra.

The user interface elements may be icons, groups of icons, selectable text-boxes, widgets, action buttons, etc. The user interface elements are selectable. Depending on the user input interface used, the selection may involve clicking on the user interface elements with a mouse pointer when using a mouse, touching the user interface elements when using a touch screen, etc. The actions associated with the user interface elements are themselves associated with the interactive inspection of the region of interest, and may comprise adjusting display of the region of interest, performing a measurement on the region of interest, performing image processing on the region of interest, and including information pertaining the region of interest in a report. The actions are executable on a processor, and when the associated user interface element is selected, executed on said processor.

The actions may be part of applications being executable on the processor. There may be different applications, with each application comprising different actions or different sets of actions. The applications may also share certain actions, i.e., said actions may be comprised in multiple ones of the applications. The applications may cause the display means to establish a different display configuration of the associated user interface elements for the different actions or different sets of actions. For example, one application may relate to cardiac analysis, comprise actions relating to the general inspection of a heart, and establish the associated user interface elements in a certain manner. Another application may relate to advanced ventricular analysis, comprise actions relating to the inspection of the ventricles of the heart, and establish the associated user interface elements in a different manner than the cardiac analysis application. Then, in dependence on the anatomical property, or the deviation determined from the anatomical property, one of the applications may be selected for execution. For example, when the region of interest resembles a healthy heart, the cardiac analysis application may be executed to allow the user to perform a general inspection of the heart. Moreover, when the region of interest resembles a diseased heart, the advanced ventricular analysis application may be executed to allow the user to immediately perform an advanced analysis of the functioning of the heart's ventricles.

The display configuration may be established in dependence on a correspondence between the anatomical property and the actions, with the correspondence being obtained from medical data. For example, the medical data may specify an anatomical property and actions normally associated with the interactive inspection of the region of interest given said anatomical property. The display configuration may also be established in dependence on a historical use of the actions given the anatomical property. For example, the system may record a correspondence between an anatomical property of the region of interest and a selection of actions by the user. Accordingly, having established this correspondence over time, the display configuration may be based on said correspondence. It will be appreciated that any other known technique for tailoring or optimizing a display of user interface elements to an anatomical property of a region of interest may be used as well.

The display means may be arranged for guiding the user through a medical workflow by establishing the display configuration in further dependence on a user's position in the medical workflow. A medical workflow may be a linear sequence of actions for guiding the user through an interactive inspection. The medical workflow may also be a linear sequence of work lists, i.e., lists which each comprise a number of actions to be performed as part of the interactive inspection. The medical workflow may also constitute a non-linear sequence of actions or work lists, with, e.g., an outcome of a current action affecting which action or work list is next. A single work list may constitute a medical workflow. However, a medical workflow may also be constituted by multiple work lists. The display means may be arranged for adapting the display configuration to the user's position in the medical workflow, e.g., by only showing, or more prominently showing, user interface elements that are relevant given the anatomical property and the user's position in the medical workflow. Thus, user interface elements that are of less or no relevance given the user's position in the medical workflow may be hidden or less prominently shown.

It will be appreciated that there are important diseases that distinguish themselves by abnormal organ shapes. For example, patients with coronary or artery disease may have a normally shaped heart, whereas patients experiencing heart failure may have a larger sized and/or differently shaped heart than normally. Another example is patients with severe changes in size of certain brain structures due to the progression of traumatic brain injury or Alzheimer disease. When diagnosing medical images of such patients, it may be needed to interactively inspect the medical images by viewing anatomical properties, performing measurements, selecting specific image processing options or including specific items in the report. Such steps may be different from those that must be considered for patients with a normal organ shape. Moreover, even though a clinical workstation may offer all the necessary functionality to provide the above actions, the user interface elements corresponding to said actions may not be readily accessible, e.g., being hidden in submenus.

By determining an anatomical property of a region of interest, it may be determined, when the region of interest is, e.g., an organ, whether the organ deviates from a normal (in the medical sense, i.e., healthy) organ, etc. Depending on the result, the display of the user interface elements is adapted. The adaption may be such that user interface elements on the display are arranged to allow quick access to relevant functionality, i.e., to actions that are of relevance to the interactive inspection. The result may also influence subsequent image analysis, e.g. by performing model-based segmentation with a disease-specific shape prior, or may trigger the clinical workstation to display additionally relevant information.

An example use of the present invention is in the cardiac diagnosis using a sequence of retrospectively gated Computed Tomography Angiogram (CTA) images. Such diagnosis normally involves an interactive inspection which comprises viewing the coronaries to detect stenosis and assessing of the global left ventricular function. However, in case of heart failure patients, the interactive inspection may comprise assessing local heart motion, dyssynchrony, Left Ventricular (LV) and Right Ventricular (RV) function and possibly assessing a presence of valvular disease, e.g. by in turn analyzing the left and right ventricular volume over time to quantify aortic regurgitation.

The clinical workstation may comprise a cardiac CTA diagnostic application which displays a so-termed work list for the interactive inspection. A work list may serve as a reminder to the user, e.g., the clinician, of steps to take or actions to perform during the interactive inspection. Instead of a reminder, the work list may also constitute a list of necessary steps or actions to take. The work list may represent a part of a so-termed medical or clinical guideline for diagnosis of a medical condition, and thus the steps therein may represent actions to take by the user or constitute actions for the system to perform.

The work list for a patient with a normal heart shape may include the steps of "Coronary Inspection" and "Global LV Analysis". As such, the clinician may visually inspect the coronary, and perform, using the clinical workstation, a global LV analysis.

For patients with an abnormal heart shape, the step "Global LV Analysis" may be replaced by "Global LV+RV Analysis" and the steps "Local LV Motion Analysis" and "Valve Analysis" may be added. The above steps may, at least in part, be embodied in actions performed by the clinical workstation on request of the user. For effectuating such a request, the clinical workstation may display user interface elements corresponding to said actions. Thus, when the patient has an abnormal heart shape, the display configuration of the user interface elements may differ from that of a normal heart shape, in that user interface elements for the actions for "Local LV Motion Analysis" and "Valve Analysis" may be added, and the user interface element for the action for "Global LV Analysis" may be replaced by an user interface element for "Global LV+RV Analysis". Moreover, the user interface elements may be sorted in order of their appearance in the work list.

In addition to the above displaying of the user interface elements, different or additional information may be displayed for a patient with a normal heart shape than for a heart failure patient by the applications or actions corresponding to the steps in the work list. For example, whereas LV & RV volumes and curves are shown for patients with a normal heart shape, the aortic regurgitation volume and fraction may be also computed for a patient experiencing heart failure. In the case of "Local LV Motion Analysis", wall thickening may be displayed for "normal" patients in bull eye plots, while dyssynchrony related information is displayed for heart failure patients. In addition, subsequent segmentation may be performed with separate models for the "normal" patients than for the heart failure patients.

It may be desirable to also display user interface elements of actions that are considered less relevant given the particular deviation of the region of interest, as it may be possible to err in the determining of the deviation. The less relevant user interface elements, however, may then be displayed less prominently, e.g., using submenus. Thus, in the event that the determining of the deviation of the region of interest is erroneous, the user is still provided with the user interface elements associated with any needed actions.

The deviation of the region of interest may be determined using any suitable technique from the field of image analysis and in particular medical image analysis. For example, a Hough transform may be used, and in particular, a so-termed extended Generalized Hough Transformation (GHT). To detect an abnormal shape of the region of interest with the GHT, e.g., a heart, the GHT may be performed twice: once with a Hough table constructed from patients with a normal heart shape and once with a Hough table constructed from patients with an abnormal dilated heart shape. The GHT is thus used for establishing the region of interest in the medical image. The Hough accumulators for both Hough tables constructed during detection may then be normalized, e.g., to account for a different number of entries in the Hough table. Moreover, the maxima in both accumulators may be compared to decide whether the medical image shows a normal or an abnormal heart shape. The GHT is therefore also used for the determining of the deviation of the region of interest, i.e., for purpose of discrimination of the region of interest. Instead of the GHT, however, any other suitable technique may be used as well for establishing the region of interest and/or for determining the deviation of the region of interest.

It will be appreciated that the present invention applies to diagnostic workstations, clinical decision support systems, picture archiving and communication system, imaging systems and similar workstations and systems to enhance the workflow and ease-of-use of clinical applications and to facilitate the diagnostic task of a user. Moreover, the present invention applies to terminals such as so-termed thin clients and web clients, which enable users to access clinical applications running on, or being provided by, a server. The system may be a client/server system, i.e., be constituted by a client and a server.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A medical image system comprising:
an input device;
a processor;
a database; and
a display;
wherein:
the database includes at least one reference organ and a plurality of user actions that are associated with a diagnosis of an organ based on a plurality of possible deviations of the organ with respect to the reference organ;
the processor:
provides a user-interface on the display;
receives a user selection of a region of interest in a medical image via the input device and the user-interface;
identifies a target organ in the region of interest in the medical image;
compares one or more features of the target organ to one or more features of a corresponding reference organ in the database to identify an anatomical property that is indicative of a deviation of the organ with respect to the reference organ;
determines a recommended workflow of user actions associated with the deviation from the database;
modifies the user-interface on the display to provide user interface elements corresponding to the recommended workflow of the user actions;
receives a user-selected user interface element;
executes the user action associated with the user interface element; and
provides a result of the execution of the user action on the display;
wherein the database includes a reference workflow of user actions if no deviations of the organ are diagnosed with respect to the reference organ;
wherein the recommended workflow differs from the reference workflow;
wherein the processor modifies the user-interface to provide a structure of the user interface elements that indicates a prominence of one or more of the user interface elements based on the recommended workflow; and wherein the prominence of at least one of the one or more of the user interface elements based on the recommended workflow differs from a reference prominence of the at least one of the one or more user interface elements based on the reference workflow.

2. The system of claim 1, wherein the structure of the user interface elements includes at least one of: a rank of the user interface elements in a list, a hierarchical arrangement of the user interface elements in a menu tree, and a spatial arrangement of the user interface elements on a display area.

3. The system of claim 1, wherein the database includes a level of correspondence between the anatomical property and the user actions, and the processor modifies the user interface based on the level of correspondence.

4. The system of claim 1, wherein the processor modifies the user interface to provide guidance to the user through the recommended workflow based on the user's position in the recommended workflow.

5. The system of claim 4, wherein the processor modifies the user interface to provide a level of visibility of individual ones of the user interface elements based on the user's position in the recommended workflow.

6. The system of claim 1, wherein the user actions associated with anatomical property are associated with execution of corresponding applications, and the execution of each of the applications by the processor establishes a different display configuration of the associated user interface elements.

7. The system of claim 1, wherein the user actions include at least one of: adjusting display of the region of interest, performing a measurement on the region of interest, performing image processing on the region of interest, and including information pertaining the region of interest in a report.

8. The system of claim 1, wherein the processor determines the anatomical property by applying a Hough transform to the region of interest, the Hough transform comprising using a first Hough table and a second Hough table, the first Hough table being constructed from regions of interests having the anatomical property, the second Hough table being constructed from regions of interests not having the anatomical property, and comparing Hough accumulators of both Hough tables.

9. The system of claim 1, wherein the anatomical property is indicative of the deviation in at least one of: a shape, a size, a texture and a location, of the organ.

10. A non-transitory computer-readable medium that comprises a program that, when executed by a processor, causes the processor to:

provide a user-interface on a display;

receive a user selection of a region of interest in a medical image via a user-interface;

identify a target organ in the region of interest in the medical image;

access a database that includes at least one reference organ and a plurality of user actions that are associated with a diagnosis of an organ based on a plurality of possible deviations of the organ with respect to the reference organ;

compare the target organ to the reference organ to identify an anatomical property that is indicative of a deviation of the organ with respect to the reference organ;

determine a recommended workflow of user actions associated with the deviation from the database;

modify the user-interface on the display to provide user interface elements corresponding to the recommended workflow of the user actions;

receive a user-selected user interface element;

execute the user action associated with the user interface element; and provide a result of the execution of the user action on the display;

wherein the database includes a reference workflow of user actions if no deviations of the organ are diagnosed with respect to the reference organ;

wherein the recommended workflow differs from the reference workflow;

wherein the program causes the processor to modify the user-interface to provide a structure of the user interface elements that indicates a prominence of one or more of the user interface elements based on the recommended workflow; and wherein the prominence of at least one of the one or more of the user interface elements based on the recommended workflow differs from a reference prominence of the at least one of the one or more user interface elements based on the reference workflow.

11. The medium of claim 10, wherein the structure of the user interface elements includes at least one of: a rank of the user interface elements in a list, a hierarchical arrangement of the user interface elements in a menu tree, and a spatial arrangement of the user interface elements on a display area.

12. The medium of claim 10, wherein the database includes a level of correspondence between the anatomical property and the user actions, and the program causes the processor to modify the user interface based on the level of correspondence.

13. The medium of claim 10, wherein the program causes the processor to modify the user interface to provide guidance to the user through the recommended workflow based on the user's position in the recommended workflow.

14. The medium of claim 13, wherein the program causes the processor to modify the user interface to provide a level of visibility of individual ones of the user interface elements based on the user's position in the reference workflow.

15. The medium of claim 10, wherein the user actions associated with anatomical property are associated with execution of corresponding applications, and the execution of each of the applications by the processor establishes a different display configuration of the associated user interface elements.

16. The medium of claim 10, wherein the user actions include at least one of: adjusting display of the region of interest, performing a measurement on the region of interest, performing image processing on the region of interest, and including information pertaining the region of interest in a report.

17. The medium of claim 10, wherein the program causes the processor to determine the anatomical property by applying a Hough transform to the region of interest, the Hough transform comprising using a first Hough table and a second Hough table, the first Hough table being constructed from regions of interests having the anatomical property, the second Hough table being constructed from regions of interests not having the anatomical property, and comparing Hough accumulators of both Hough tables.

18. The medium of claim 10, wherein the anatomical property is indicative of the deviation in at least one of: a shape, a size, a texture and a location, of the organ.

* * * * *